United States Patent
Hasegawa et al.

(10) Patent No.: US 7,559,888 B2
(45) Date of Patent: Jul. 14, 2009

(54) ENDOSCOPE INSERTION DIRECTION DETECTING SYSTEM

(75) Inventors: Jun Hasegawa, Hino (JP); Tetsuo Nonami, Hino (JP)

(73) Assignee: Olympus Corporation, Tokyo (JP)

( * ) Notice: Subject to any disclaimer, the term of this patent is extended or adjusted under 35 U.S.C. 154(b) by 669 days.

(21) Appl. No.: 10/531,496

(22) PCT Filed: Nov. 19, 2003

(86) PCT No.: PCT/JP03/14711

§ 371 (c)(1),
(2), (4) Date: Apr. 15, 2005

(87) PCT Pub. No.: WO2004/045397

PCT Pub. Date: Jun. 3, 2004

(65) Prior Publication Data

US 2006/0015011 A1    Jan. 19, 2006

(30) Foreign Application Priority Data

Nov. 20, 2002    (JP) .............................. 2002-337001

(51) Int. Cl.
*A61B 1/04* (2006.01)
(52) U.S. Cl. ........................ 600/117; 600/118; 600/921; 348/65
(58) Field of Classification Search ................ 600/117, 600/118, 109, 103, 921; 348/65; 382/128, 382/190, 203
See application file for complete search history.

(56) References Cited

U.S. PATENT DOCUMENTS

| 4,916,533 | A | | 4/1990 | Gillies et al. |
| 5,018,509 | A | * | 5/1991 | Suzuki et al. ............... 600/115 |
| 5,347,987 | A | * | 9/1994 | Feldstein et al. ............ 600/109 |
| 5,658,238 | A | | 8/1997 | Suzuki et al. |

FOREIGN PATENT DOCUMENTS

| GB | 2 227 836 A | 8/1990 |
| JP | 2-182231 | 7/1990 |
| JP | 2680111 | 8/1997 |
| JP | 2003-093328 | 4/2003 |

* cited by examiner

*Primary Examiner*—John P Leubecker
(74) *Attorney, Agent, or Firm*—Scully, Scott, Murphy & Presser, P.C.

(57) ABSTRACT

The invention provides an endoscope inserting direction detecting apparatus and method with which the direction of a lumen can be determined reliably despite a simple configuration. The endoscope inserting direction detecting apparatus includes a pixel sampling unit that samples a stated pixel value from each of domains constituting an endoscopic image received by an image input/output control circuit; a shape-of-range estimating unit that estimates the shape of a range within the endoscopic image according to the continuity of the distribution of the pixels indicating the stated pixel value; and an inserting direction determining unit that determines an inserting direction within a body cavity, in which an endoscope should be further inserted, on the basis of the estimated shape. The inserting direction is displayed together with the endoscopic image.

6 Claims, 14 Drawing Sheets

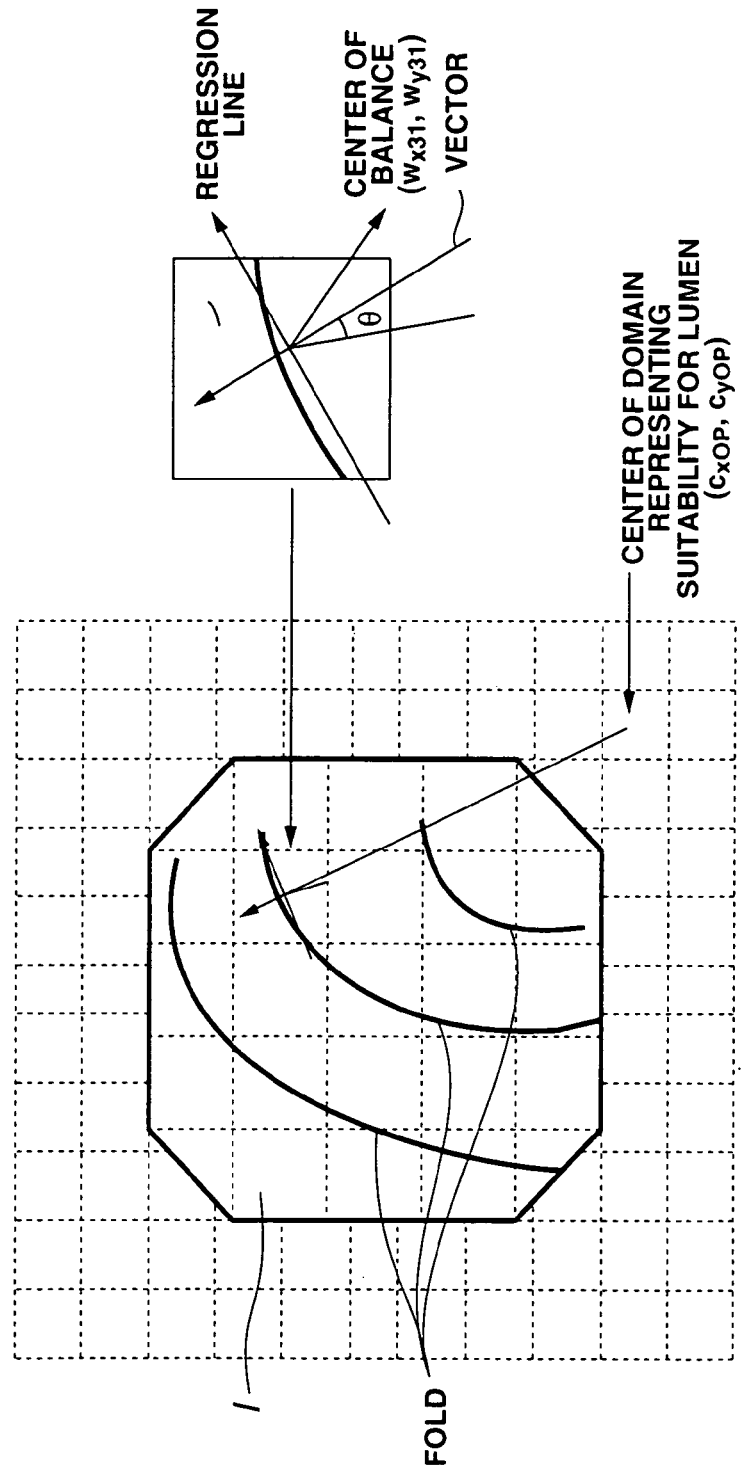

ENDOSCOPE INSERTION DIRECTION DETECTING SYSTEM

TECHNICAL FIELD

The present invention relates to an endoscope inserting direction detecting apparatus, an endoscope inserting direction detecting system, and an endoscope inserting direction detecting method that when an endoscope insertion unit is inserted into a body cavity that has a complexly tortuous structure, detect an inserting direction according to the shape of the body cavity.

BACKGROUND ART

In the past, endoscope systems including an endoscope whose insertion unit that is elongated and flexible is inserted into a body cavity in order to observe the inside of the body cavity or to, if necessary, collect or cure a tissue in an intracavitary region have been widely adopted.

When the insertion unit of the endoscope included in the endoscope system is inserted into a body cavity, an intracavitary shape and an inserting direction must be judged from an endoscopic image to be seen. Operators are therefore required to be experienced in inserting the insertion unit. For example, assuming that endoscopic examination is performed on the large intestine, the shape of the large intestine is complex and the lumen thereof is narrow and different from person to person. Moreover, when the insertion unit approaches a bent region (sigmoid colon, hepatic curvature, splenic curvature, or the like), an intestinal wall, or an intestinal fold, it becomes hard to determine an inserting direction. The operators are therefore requested to get highly skilled and experienced in inserting the insertion unit.

Conventional endoscopes require the advanced skill and experience of insertion. An endoscope inserting direction detecting apparatus capable of displaying the direction of a lumen, that is, an endoscope inserting direction has therefore been proposed.

For example, an endoscope inserting direction detecting method has been proposed (refer to, for example, Japanese Patent No. 2680111). Herein, a gradient in a change rate at which a quantity characteristic of an endoscopic image changes is compared with a predefined reference value. Points in the endoscopic image at which the gradients are equal to or larger than a predetermined value are sampled as discontinuous points, whereby an object image is produced. The produced object image is divided into a plurality of domains. Suitability for segments are sampled from the respective domains according to a modified Hough transform method. The sampled suitability for segments are divided into groups on a sensory basis according to a predefined criterion, whereby an optimal suitability for a segment is selected. The information on the optimal segment is regarded as a child node, and the sum of a plurality of child nodes or segments is regarded as a parent node or a stripe segment. Finally, the child node concerning the optimal segment is sequentially selected. Resultant small domains are concatenated as start segments of segments. Based on the pattern of the concatenated segments, suitability for segments located at deeper positions are selected in order to determine an endoscope inserting direction.

Moreover, conventional endoscope inserting direction detecting methods include a method proposed in Japanese Unexamined Patent Application Publication No. 2003-93328. According to the proposed method, M sample pixels are selected from a red component of an endoscopic image. Gradient vectors are calculated in order to determine the direction of a gradient in the brightness levels indicated by the sample pixels. The direction of a lumen is then calculated based on the gradient vectors, and indicated with an arrow mark superposed on the endoscopic image.

According to the endoscope inserting direction detecting method proposed in the Japanese Patent No. 2680111, an endoscopic image of the large intestine from which representatives of edges are sampled is divided into a plurality of domains. A representative of an edge useful in detecting the direction of a lumen is detected from each of the domains according to the modified Hough transform. The detected representatives of the edge are concatenated in order to detect the shape of a fold. Consequently, the direction of the lumen is estimated. The process is complex and hard to be executed in real time.

Moreover, the endoscope inserting direction detecting method proposed in the Japanese Unexamined Patent Application Publication 2003-93328 has a drawback. Namely, a halation is sampled from an endoscopic image of the large intestine, and expressed with thin lines. The shape determined with the thin lines is sampled, and a perpendicular at the midpoint of a segment determined with two sampled points is defined. The direction of a lumen is estimated from a position at which a plurality of resultant perpendiculars at the midpoints of segments is converged. If the perpendiculars are not converged at one point, the position of a lumen cannot be determined.

The present invention attempts to break through the foregoing circumstances. An object of the present invention is to provide an endoscope inserting direction detecting apparatus, an endoscope inserting direction detecting system, and an endoscope inserting direction detecting method capable of reliably detecting the direction of a lumen using a simple configuration.

DISCLOSURE OF INVENTION

An endoscope inserting direction detecting apparatus in accordance with the present invention comprises: image input means for receiving an endoscopic image from an endoscope that is inserted into a body cavity; pixel sampling means for sampling a stated pixel value from the endoscopic image received by the image input means; shape-of-range estimating means for estimating the shape of a specified area from the continuity in the distribution of the pixels that represent the stated pixel value and that are sampled by the pixel sampling means; and inserting direction determining means for determining an inserting direction within the body cavity, in which the endoscope should be further inserted, on the basis of the shape determined by the shape-of-range estimating means.

Owing to the endoscope inserting direction detecting apparatus in accordance with the present invention, an inserting direction within a body cavity can be reliably and highly precisely detected using an endoscopic image. The detected inserting direction is displayed together with the endoscopic image, whereby an endoscope can be manipulated smoothly irrespective of experience in endoscopic examination.

An endoscope inserting direction detecting system comprises: endoscopic image dividing means for dividing an endoscopic image, which is produced by an endoscope that is inserted into a body cavity, into a plurality of domains; pixel sampling means for comparing values, which are indicated by pixels constituting each of the plurality of domains into which the endoscopic image is divided by the endoscopic image dividing means, with a threshold, and sampling the distribution of pixels whose values are equal to or larger than the threshold; suitability-for-lumen position designating means for defining domains that represent suitability for a lumen position; direction-of-lumen estimating means for defining a plurality of circles of which radii are different from one another and which are extended over the domains representing suitability for a lumen position defined by the suitability-for-lumen position defining means and the domains of the endoscopic image, and for estimating the direction of a lumen from the distribution of pixels which are sampled by the pixel sampling means because their values are equal to or larger than the threshold and which are placed between the plurality of circles; inserting direction determining means for determining an endoscope inserting direction over the domains, which represent suitability for a lumen position, according to the direction of a lumen estimated by the direction-of-lumen estimating means; and inserting direction display means on which the inserting direction is displayed together with the endoscopic image on the basis of the endoscope inserting direction determined by the inserting direction determining means.

An endoscope inserting direction detecting method comprises: image input means for receiving an endoscopic image; pixel sampling means for sampling pixels representing a high pixel value from the endoscopic image received by the image input means; pixel selecting means for selecting pixels, which lie in a specified area, from among the pixels sampled by the pixel sampling means; inserting direction determining means for determining an endoscope inserting direction on the basis of the shape of the specified area and the pixels selected by the pixel selecting means; and display means on which the inserting direction determined by the inserting direction determining means is displayed.

BRIEF DESCRIPTION OF THE DRAWINGS

FIG. 22 is an explanatory diagram concerning determination of an inserting direction within a lumen from an endoscopic image which is performed by the endoscope inserting direction detecting apparatus in accordance with the third embodiment of the present invention.

BEST MODE FOR CARRYING OUT THE INVENTION

Figure 1:
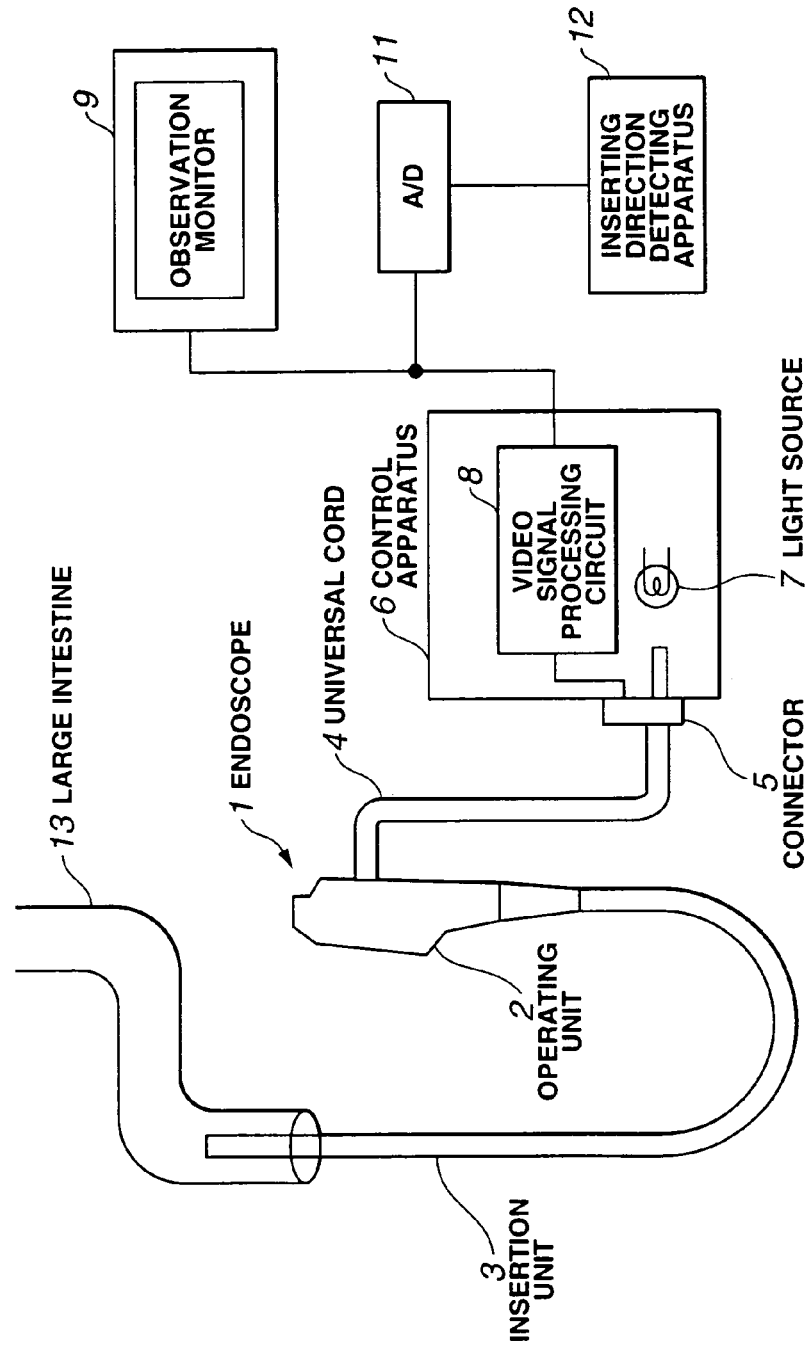
FIG. 1 is a block diagram showing the overall configuration of an endoscope system employing an embodiment of the present invention.

Referring to the drawings, embodiments of the present invention will be described below. A first embodiment of an endoscope inserting direction detecting apparatus in accordance with the present invention will be described in conjunction with FIG. 1 to FIG. 12.

Figure 2:
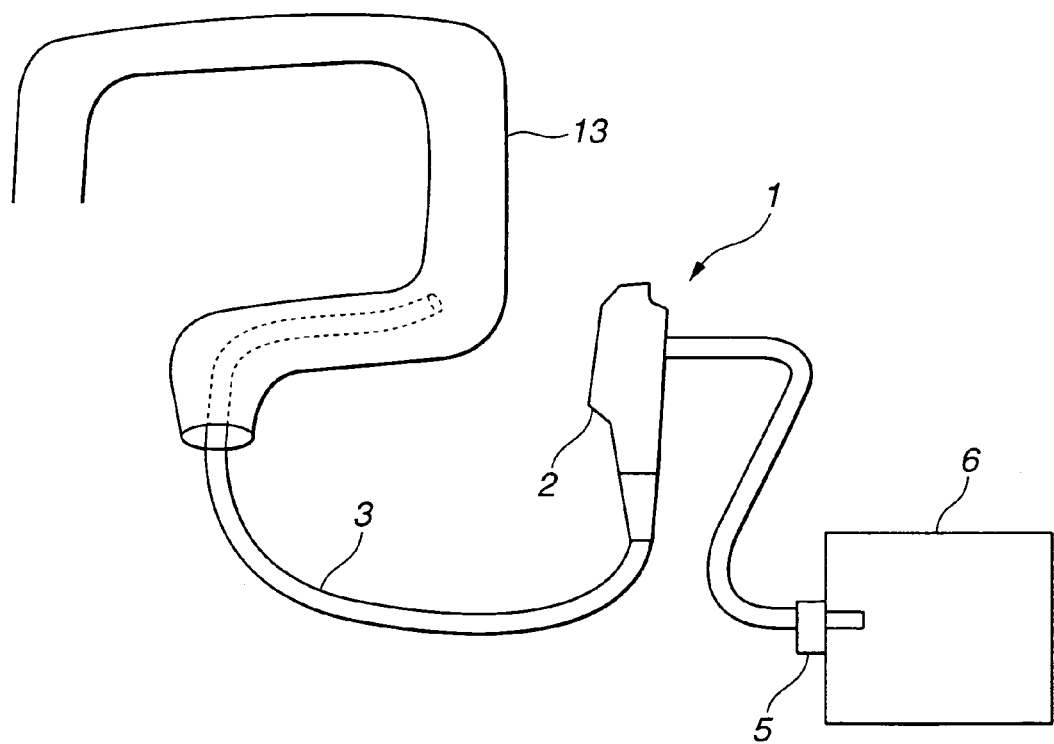
FIG. 2 is an explanatory diagram showing insertion of an endoscope, which is included in the endoscope system employing the embodiment of the present invention, into a lumen.
Figure 3:
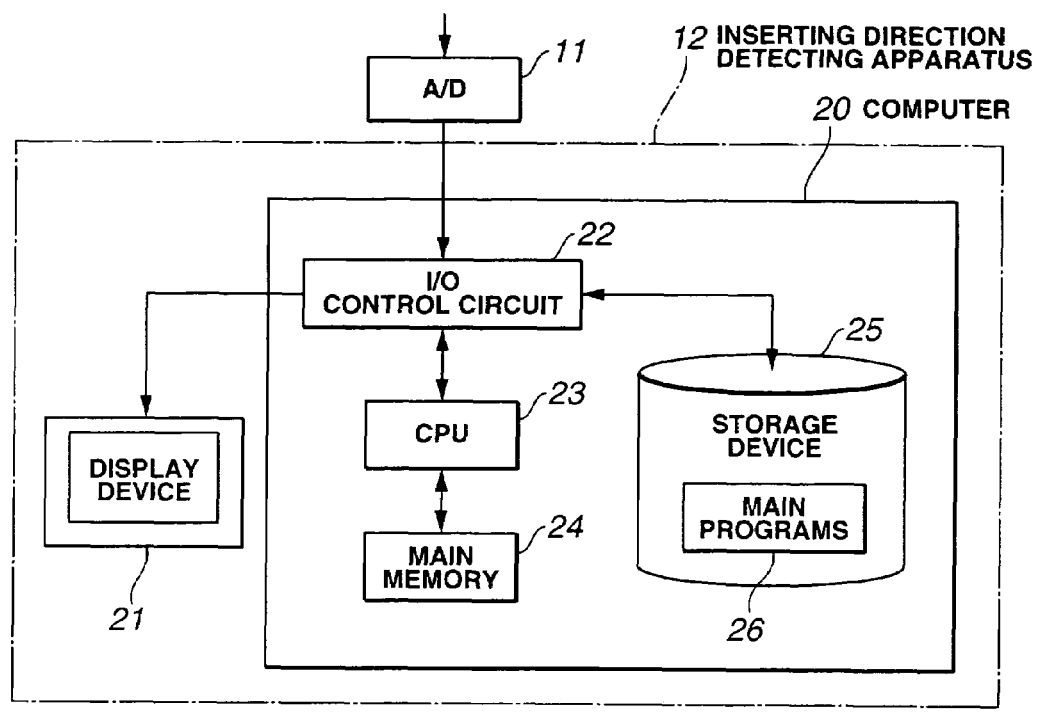
FIG. 3 is a block diagram showing the configuration of an endoscope inserting direction detecting apparatus in accordance with a first embodiment of the present invention.
Figure 4:
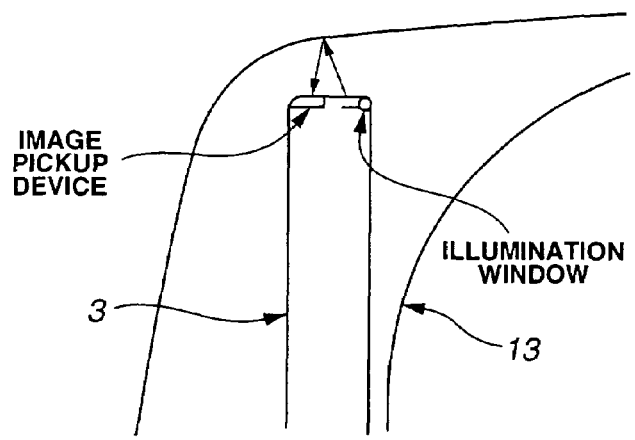
FIG. 4 is an explanatory diagram showing a bend of a lumen into which the endoscope that is included in the endoscope system employing the embodiment of the present invention is inserted.
Figure 5:
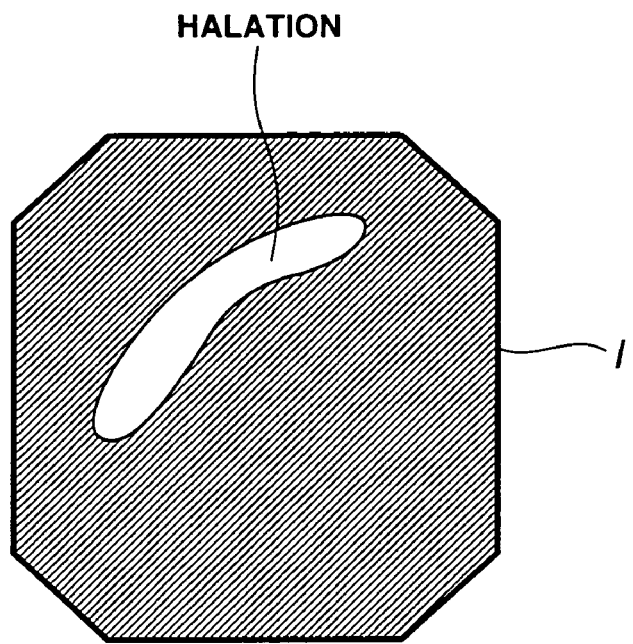
FIG. 5 is an explanatory diagram showing an image picked up image of the inside of a lumen which is formed by the endoscope system employing the embodiment of the present invention.
Figure 6:
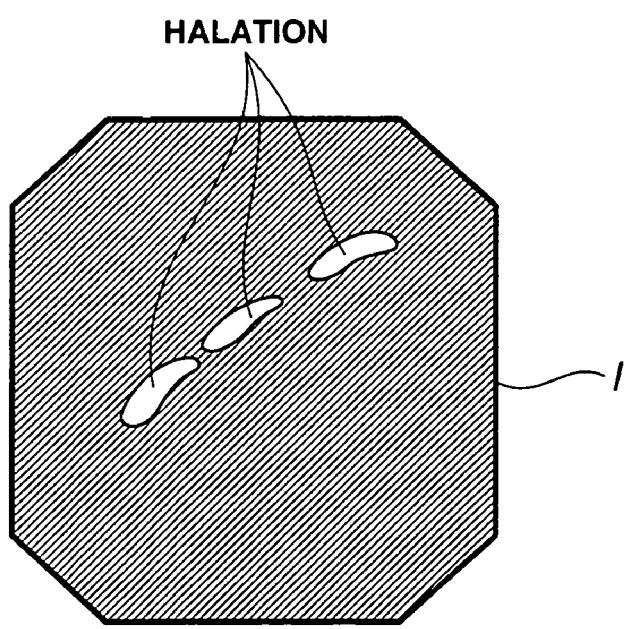
FIG. 6 is an explanatory diagram showing an image picked up image of the inside of a lumen which is formed by the endoscope system employing the embodiment of the present invention.
Figure 7:
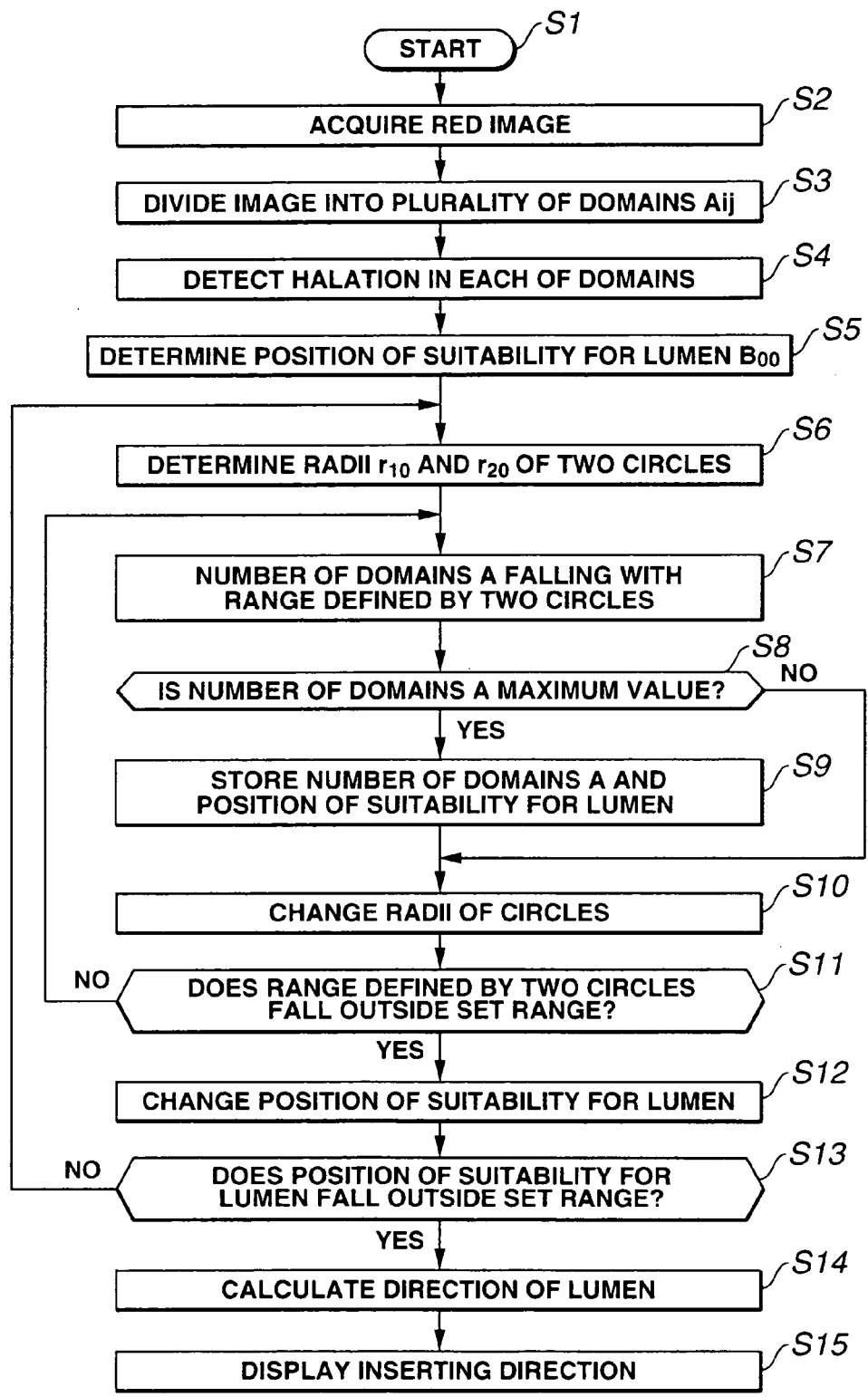
FIG. 7 is a flowchart describing actions to be performed in the endoscope inserting direction detecting apparatus in accordance with the first embodiment of the present invention.
Figure 8:
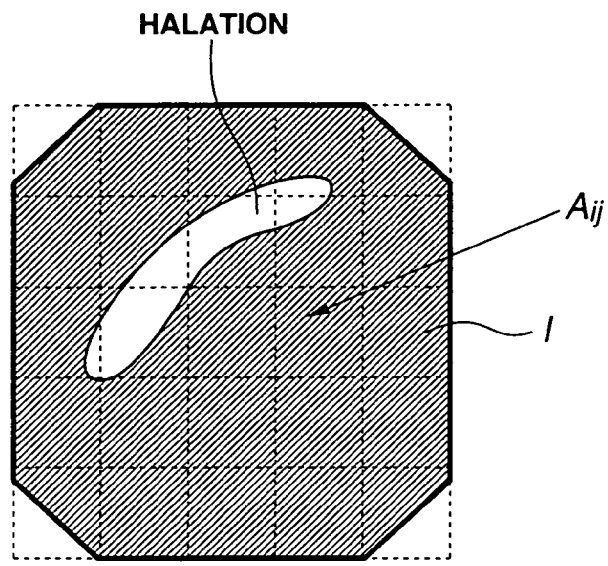
FIG. 8 is an explanatory diagram showing an example of division of an endoscopic image into a plurality of domains by the endoscope inserting direction detecting apparatus in accordance with the first embodiment of the present invention.
Figure 9:
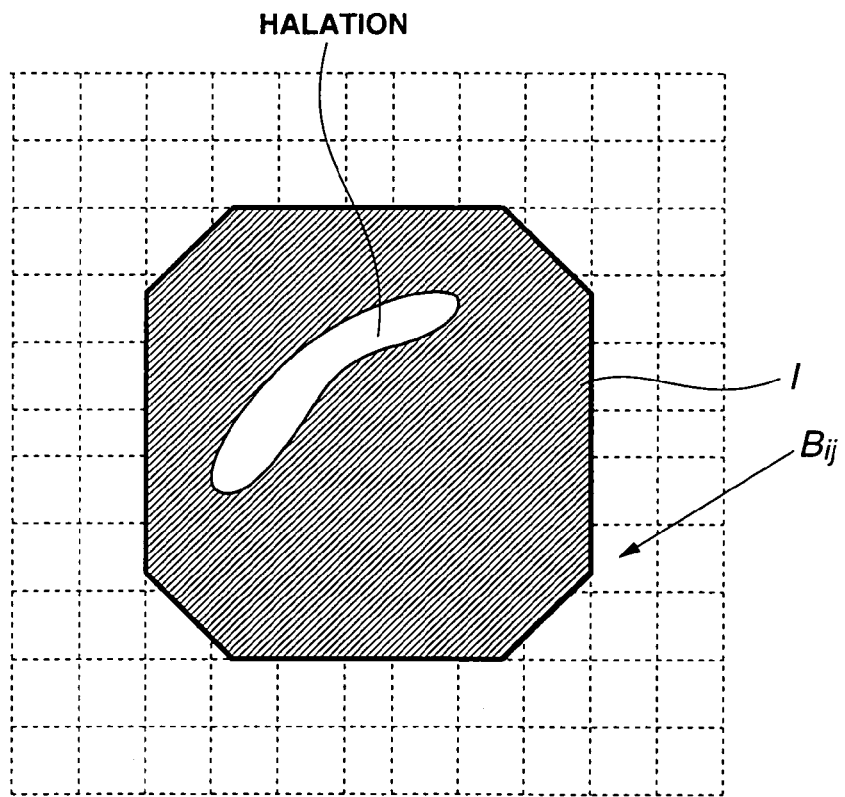
FIG. 9 is an explanatory diagram showing domains that represent suitability for a lumen and that are defined on the perimeter of the endoscopic image by the endoscope inserting direction detecting apparatus in accordance with the first embodiment of the present invention.
Figure 10:
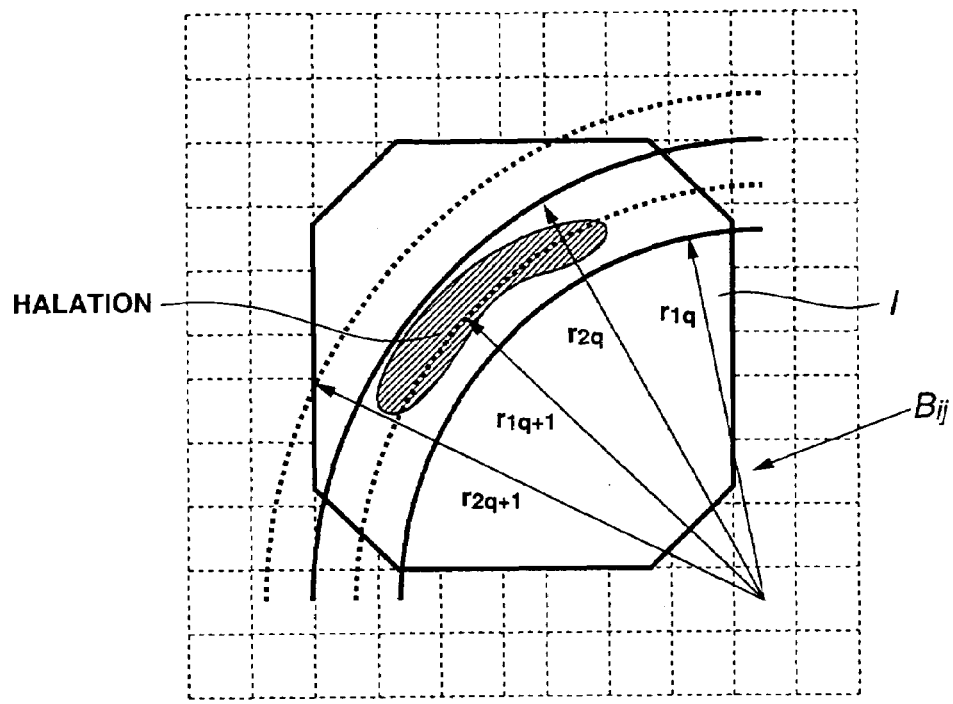
FIG. 10 is an explanatory diagram concerning determination of the direction of a lumen based on an endoscopic image which is performed by the endoscope inserting direction detecting apparatus in accordance with the first embodiment of the present invention.
Figure 11:
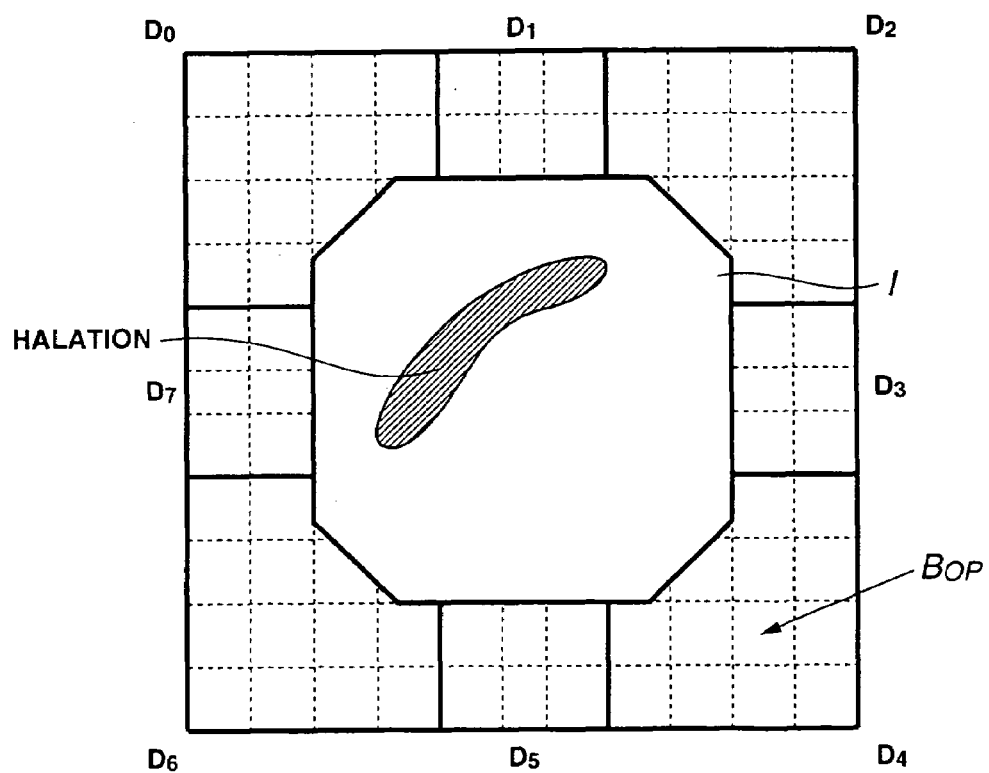
FIG. 11 is an explanatory diagram concerning determination of an inserting direction based on an endoscopic image and domains representing suitability for a lumen which is performed by the endoscope inserting direction detecting apparatus in accordance with the first embodiment of the present invention.
Figure 12:
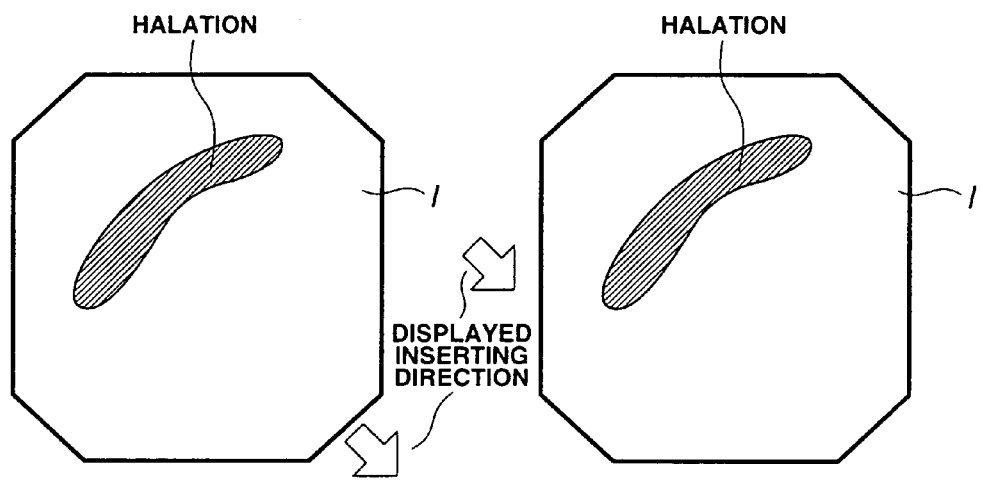
FIG. 12 is an explanatory diagram concerning an example of display of an endoscope inserting direction, which is detected by the endoscope inserting direction detecting apparatus in accordance with the first embodiment of the present invention, together with an endoscopic image.

FIG. 1 is a block diagram showing the overall configuration of an endoscope system employing an embodiment of the present invention. FIG. 2 is an explanatory diagram concerning insertion of an endoscope, which is included in the endoscope system employing the embodiment of the present invention, into a lumen. FIG. 3 is a block diagram showing the configuration of the endoscope inserting direction detecting apparatus in accordance with the first embodiment of the present invention. FIG. 4 is an explanatory diagram showing a bend of a lumen into which the endoscope that is included in the endoscope system employing the first embodiment of the present invention is inserted. FIG. 5 is an explanatory diagram showing an image picked up image of the inside of a lumen formed by the endoscope system employing the first embodiment of the present invention. FIG. 6 is an explanatory diagram showing an image picked up image of the inside of a lumen formed by the endoscope system employing the first embodiment of the present invention. FIG. 7 is a flowchart describing actions to be performed by the endoscope inserting direction detecting apparatus in accordance with the first embodiment of the present invention. FIG. 8 is an explanatory diagram showing an example of division of an endoscopic image into a plurality of domains which is performed by the endoscope inserting direction detecting apparatus in accordance with the first embodiment of the present invention. FIG. 9 is an explanatory diagram showing domains that represent suitability for a lumen and that are defined on the perimeter of an endoscopic image by the endoscope inserting direction detecting apparatus in accordance with the first embodiment of the present invention. FIG. 10 is an explanatory diagram concerning determination of the direction of a lumen based on an endoscopic image which is performed by the endoscope inserting direction detecting apparatus in accordance with the first embodiment of the present invention. FIG. 11 is an explanatory diagram concerning determination of an inserting direction based on the endoscopic image and the domains representing suitability for a lumen which is performed by the endoscope inserting direction detecting apparatus in accordance with the first embodiment of the present invention. FIG. 12 is an explanatory diagram showing an example of display of the endoscope inserting direction, which is detected by the endoscope inserting direction detecting apparatus in accordance with the first embodiment of the present invention, together with the endoscopic image.

To begin with, the overall configuration of an endoscope system employing the embodiment of the present invention will be described in conjunction with FIG. 1. The endoscope system comprises an endoscope 1, a control apparatus 6, an observation monitor 9, an analog-to-digital (hereinafter A/D) converter 11, and an endoscope inserting direction detecting apparatus (hereinafter, an inserting direction detecting apparatus) 12.

The endoscope 1 comprises an operating unit 2 and an insertion unit 3 that is elongated and flexible. A solid-state image pickup device (hereinafter, a CCD) and an end of a light guide cable from which illumination light is radiated are incorporated in the distal section of the insertion unit 3, though they are not shown. A signal cable over which a signal with which the CCD is driven or controlled is transmitted, a signal cable over which an image signal produced by the CCD is transmitted, and a light guide cable over which illumination light is propagated are run through the insertion unit 3 and operating unit 2. The endoscope 1 is connected to the control apparatus 6 via a connector 5 over a universal code 4 containing the signal cables and light guide cable.

Moreover, the insertion unit 3 has a bending section formed near the distal section thereof, though the bending section is not shown. The bending section can be bent upward, downward, rightward, or leftward. Wires used to bend the bending section are extended from the insertion unit 3 to the operating unit 2. The proximal ends of the wires are coupled to an angling knob that is included in the operating unit 2 and that is not shown.

Namely, the bending section of the insertion unit 3 is bent by manipulating the angling knob of the operating unit 2.

The control apparatus 6 comprises: a video signal processing circuit 8 that produces and transmits a signal with which the CCD is driven or controlled, that performs predetermined processing on an image pickup signal produced by the CCD so as to produce an RGB image signal which is a video signal conformable to the RGB standard and which represents an endoscopic image; a light source 7 that is a lamp for introducing illumination light to the light guide cable; and a lamp lighting control circuit.

The RGB image signal produced by the video signal processing circuit 8 included in the control apparatus 6 is transmitted to the observation monitor 9, whereby the endoscopic image is displayed. Moreover, the A/D converter 11 converts the analog RGB image signal into a digital RGB image signal. The inserting direction detecting apparatus 12 treats the digital RGB image signal so as to detect an inserting direction in which the insertion unit 3 of the endoscope 1 should be inserted, and displays the detected inserting direction on a display device that will be described later.

Inserting the insertion unit of the endoscope included in the endoscope system, which has the foregoing components, into a body cavity, for example, into the lumen of the large intestine will be described in conjunction with FIG. 2.

For endoscopic examination of the large intestine 13, the large intestine 13 is imaged using the CCD incorporated in the distal section of the insertion unit 3 of the endoscope 1. The video signal processing circuit 8 produces an RGB image signal that is a video signal conformable to the RGB standard. An endoscopic image is reproduced based on the RGB image signal and displayed on the observation monitor 9. While looking at the endoscopic image, an operator manipulates the angling knob of the operating unit 2. While bending the bending section of the insertion unit 3 upward, downward, rightward, or leftward, the operator inserts the insertion unit into the large intestine 13 until the distal section reaches the ileocecum (the portions of the small and large intestines that are taken as a whole).

The RGB image signal produced by the video signal processing circuit 8 is converted from an analog form into a digital form by the A/D converter 11, and then transmitted to the inserting direction detecting apparatus 12.

The inserting direction detecting apparatus 12 comprises: as shown in FIG. 3, a computer 20 that performs a series of operations relevant to detection of an inserting direction according to the RGB image signal that has been produced by the video signal processing circuit 8 and converted into the digital form by the A/D converter 11; and a display device 21 on which the inserting direction resulting from the operations performed by the computer 20 is displayed. The computer 20 comprises: a storage device 25 in which various main programs 26 including a program for detecting an endoscope inserting direction are stored; a central processing unit (hereinafter, a CPU) 23 that runs one of the main programs 26 residing in the memory 25 so as to execute inserting direction detection; a main memory 24 in which the results of processing executed by the CPU 23 are stored; and an input/output (hereinafter I/O) control circuit 22 that controls various inputs or outputs received from or transmitted to the A/D converter 11, display device 21, or storage device 25.

Incidentally, the main programs 26 stored in the storage device 25 include a program that is run in order to perform a series of operations for detecting an endoscope inserting direction and that is a constituent feature of the present invention. Moreover, the main programs 26 include a program to be run in order to issue a request for acquisition of an RGB image signal from the A/D converter 11 to the I/O control circuit 22 or to issue a request for display of the result of inserting direction detection on the display device 21.

The A/D converter 11 converts an RGB image signal from an analog form to a digital form. At this time, color signals of red, green, and blue are each quantized into a level that ranges from 0 to 255 and that is expressed with eight bits. The size of an image represented by the RGB image signal shall be expressed with a size ISX in a horizontal direction and a size ISY in a vertical direction. Moreover, hereinafter, the position of a pixel located at the left upper corner of an endoscopic image I shall be represented with coordinates (0,0), and the position of a pixel located at the right lower corner thereof shall be represented with coordinates (ISX-1, ISY-1).

During endoscopic examination to be performed using the endoscope system having the foregoing configuration, the mucosal surface of the portion of the large intestine right opposed to the distal section of the insertion unit 3 of the endoscope 1 strongly and specularly reflects illumination light projected from the distal end of the insertion unit 3. The reflected illumination light incident on the CCD is therefore much brighter than light reflected from the surrounding portions of the large intestine. A component of an image pickup signal produced by the CCD, which represents light returned due to specular reflection, may be saturated or may indicate a larger luminance level than the other component that represents light returned from the surrounding portions. Consequently, a phenomenon generally referred to as a halation takes place. An arc-shaped halation or halations juxtaposed like an arc appear in an image of the luminal large intestine.

Specifically, after the insertion unit 3 of the endoscope 1 is, as shown in FIG. 4, inserted into the large intestine 13, when the insertion unit 3 reaches a bent portion of the large intestine, illumination light projected from an illumination window formed on the distal end of the insertion unit 3 is specularly reflected from the mucosal surface of the bent portion of the large intestine 13. The reflected light falls on the CCD, whereby an image pickup signal is produced. The video signal processing circuit 8 included in the control apparatus 6 then produces a video signal from the image pickup signal produced by the CCD. An endoscopic image reproduced and displayed on the observation monitor 9 according to the video signal suffers from an arc-shaped halation like the one shown in FIG. 5 or halations juxtaposed like an arc like the ones shown in FIG. 6.

The possibility that a lumen is found in a direction equivalent to the direction of the center of a circle including an arc defined by an arc-shaped halation is high. Therefore, an experienced operator uses the shape of a halation or the distribution of halations as insertion aid information to judge or determine an endoscope inserting direction in which the endoscope should be inserted. For example, if the halation or halations like the one or ones shown in FIG. 5 or FIG. 6 take place, the operator judges that the lumen will be found in a direction equivalent to the direction of the right lower part of a screen. The operator angles the insertion unit 3 so that the distal section of the insertion unit 3 will be advanced in a direction equivalent to the direction of the right lower part of the screen.

As mentioned above, an arc-shaped halation or halations juxtaposed like an arc that affect an endoscopic image produced by the CCD are utilized. Namely, the inserting direction detecting apparatus 12 detects a halation by checking a pixel value indicated by pixels constituting an endoscopic image, and then displays the direction of a lumen estimated from the shape of the halation together with the endoscopic image. The actions to be performed by the inserting direction detecting apparatus 12 will be described in conjunction with FIG. 7.

Detection of an inserting direction based on an image pickup signal produced by the CCD is executed by running one of the main programs 26 stored in advance in the storage device 25 incorporated in the computer 20 included in the inserting direction detecting apparatus 12.

Specifically, the insertion unit 3 of the endoscope 1 is inserted into the large intestine, and the CCD incorporated in the distal section of the insertion unit 3 is driven. An RGB image signal produced by the video signal processing circuit 8 is converted into a digital RGB image signal by the A/D converter 11, and transferred to the inserting direction detecting apparatus 12. The CPU 23 incorporated in the computer 20 included in the inserting direction detecting apparatus 12 drives or controls the I/O control circuit 22 so as to fetch the digital RGB image signal. Moreover, the CPU 23 reads one of the main programs 26 from the storage device 25 so as to execute endoscope inserting direction detection.

Moreover, based on the digital RGB image signal produced by the A/D converter 11 and fetched from the I/O control circuit 22 driven by the CPU 23, an endoscopic image affected by a halation is displayed on the display device 21 like the observation monitor 9.

Endoscope inserting direction detection is invoked when the CPU 23 reads an endoscope inserting direction detection program that is one of the main programs 26 at step S1. At step S2, the CPU 23 drives or controls the I/O control circuit 22 and acquires a red component from the digital RGB image signal produced by the A/D converter 11.

According to the first embodiment, the red component of the RGB image signal is used to execute endoscope inserting direction detection. Aside from the red signal component, the green signal component, blue signal component, or luminance signal component (0.3R+0.6G+0.1B) or the like may be used to execute endoscope inserting direction detection.

Thereafter, at step S3, the CPU 23 divides the red image signal, which is acquired at step S2, into a plurality of domains. For the division of the red image signal into domains to be performed at step S3, an endoscopic image I is, as indicated with dot lines in FIG. 8, divided into a plurality of domains Aij ($0 \leq i < 1$, $0 \leq j < m$).

Thereafter, at step S4, the CPU-23 detects a halation in each of the domains Aij into which the image is divided at step S3. In order to detect a halation in each of the domains Aij, specifically, a binary image H is produced based on the values r(x,y) of pixels which constitute the endoscopic image I and whose positions are represented with coordinates (x,y)

$(0 \leq x < Isx, 0 \leq y < Isy)$. The value of each pixel $h(x,y)$ contained in the binary image H is calculated according to an expression (1) below.

$$h(x,y)=1 \text{ if } r(x,y) \geq THL \quad (1)$$

$$h(x,y)=0 \text{ if } r(x,y) < THL \quad (2)$$

where THL denotes a threshold and equals 255. Even when the value of a pixel does not reach 255, the pixel may be discerned as a point of halation. Therefore, the threshold is set to an appropriate value. Incidentally, if the number of pixels each discerned as a point of halation and contained in one domain Aij is small, the values of pixels containing in the domain of the binary image H are calculated according to an expression (2) $h(x,y)=0$ instead of the expression (1) $h(x,y)=1$. Consequently, a pinpoint halation is removed and only a halation useful in detecting the direction of a lumen is detected.

Namely, a pixel value indicated by each of the pixels constituting each of the domains Aij is compared with the threshold THL in order to detect a halation.

Thereafter, at step S5, the CPU 23 defines the positions of suitability for a lumen. In order to define the positions of suitability for a lumen, as indicated with dot lines in FIG. 9, domains Bij ($0 \leq i < O$, $0 \leq j < P$) representing suitability for a lumen are defined on the perimeter of the endoscopic image I.

After the CPU 23 completes defining of the positions of suitability for a lumen at step S5, the CPU 23 defines two circles r1q and r2q that have different radii but have the centers thereof located at the position of the center of a domain Bij representing suitability for a lumen as shown in FIG. 10. At step S7, the CPU 23 calculates the number of domains Aij of the endoscopic image I that represent a halation and that fall within a range defined with the two circles.

The number of domains Aij, which represent a halation and fall within the range defined with the two circles, calculated at step S7 is checked at step S8 to see if the number of domains is a maximum value. If the number of domains is judged as the maximum value, the number of domains Aij representing a halation and the position Bij of suitability for a lumen are stored at step S9.

If the number of domains Aij is judged not to be the maximum value at step S8, or if storing the number of domains Aij representing a halation and the position Bij of suitability for a lumen at step S9 is completed, the CPU 23 changes the radii of the two circles defined at step S6 into r1q+1 and r2q+1 respectively, at step S10 as shown in FIG. 10. The CPU 23 judges at step S11 whether a range defined with the new two circles extends outside the domains Aij constituting the endoscopic image I. If the range defined with the new two circles is judged to extend inside the domains Aij constituting the endoscopic image I, control is returned to step S7. Step S7 to step S11 are resumed. If the range defined with the new two circles is judged to extend outside the domains Aij constituting the endoscopic image I, the position Bij of suitability for a lumen is changed at step S12.

At step S13, the CPU 23 judges whether the new position Bij of suitability for a lumen into which the previous position is changed at step S12 falls outside a range of positions of suitability for a lumen. If the new position Bij of suitability for a lumen is judged to fall within the range of positions of suitability for a lumen, control is returned to step S6. Step S6 to step S12 are resumed. If the new position Bij of suitability for a lumen is judged to fall outside the range of positions of suitability for a lumen, the domains Bij representing suitability for a lumen are, as shown in FIG. 11, grouped into, for example, eight domains Di ($0 \leq i < 8$). A domain Di containing the position Bij of suitability for a lumen stored at step S9 is then identified.

Assuming that the position Bij of suitability for a lumen determined at step S12 is a position Bop shown in FIG. 11, the position Bop is contained in a domain D4. In other words, an inserting direction within a lumen in which the insertion unit 3 should be further inserted is equivalent to the direction of the domain D4 that is the direction of the right lower part of FIG. 11. At step S15, the inserting direction is presented while being superposed on the endoscopic image displayed on the display device 21.

When it says that an inserting direction is displayed, it means that, as shown in FIG. 12, arrow marks indicating the inserting direction may be displayed on the perimeter of the endoscopic image I displayed on the display device 21. Otherwise, the arrow marks indicating the inserting direction may be displayed while being superposed on the endoscopic image I, though the superposed arrow marks are not shown.

According to the first embodiment, since a range defined with two circles is narrowed, a halation shaped more greatly like an arc can be detected. Moreover, since the domains Bij representing suitability for a lumen are finely defined, the position of a lumen can be estimated highly precisely.

As described above, according to the first embodiment, even if a plurality of halations occurs, the position of a lumen can be estimated on a stable basis irrespective of the shape of each halation. Moreover, it is judged whether a specified area is useful in detecting the position of a lumen on the basis of the number of pixels representing a halation and being contained in the specified area. Therefore, small halations like noises can be removed. Consequently, the position of a lumen can be estimated on the stable basis.

Figure 13:
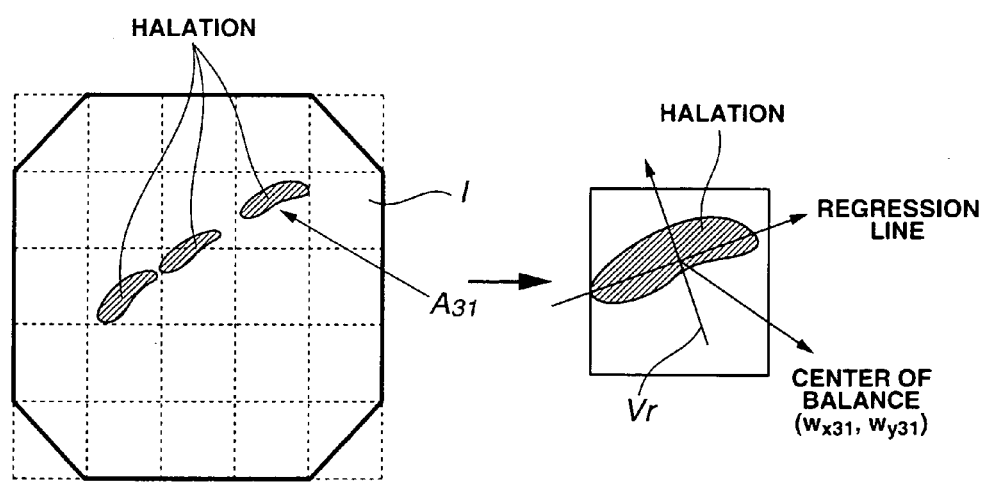
FIG. 13 is an explanatory diagram concerning detection of the position of a halation using an endoscopic image which is performed by an endoscope inserting direction detecting apparatus in accordance with a second embodiment of the present invention.

Next, an endoscope inserting direction detecting apparatus in accordance with a second embodiment of the present invention will be described in conjunction with FIG. 13 and FIG. 14. Incidentally, the configuration of the endoscope inserting direction detecting apparatus in accordance with the second embodiment and the process of estimating the position of a lumen as an inserting direction are fundamentally identical to those of the first embodiment. A difference from the first embodiment lies in a method of calculating the number of domains Aij at step S7.

According to the first embodiment, at step S7, the number of domains Aij representing a halation and falling within a range defined by two circles (r1q and r2q) is calculated. According to the second embodiment, whether the domains Aij representing a halation and falling within a range defined by two circles are useful in detecting the direction of a lumen is judged. The number of only domains Aij representing the halation and being judged to be useful in detecting the direction of a lumen is calculated.

For evaluation of the shape of a halation, a distribution of pixels representing the halation and being contained in each of the domains Aij is checked. Specifically, for example, as shown in FIG. 13, the position of a center of balance W31 (Wx31, Wy31) of a halation represented by a domain A31 is calculated from the coordinates of the positions of pixels, which represent the halation and are detected using a threshold, according to the following expressions (3) and (4):

$$W_{x31} = \frac{1}{s}\sum_{k}^{s} X_k \quad (3)$$

-continued $$W_{y31} = \frac{1}{s}\sum_{k}^{s} Y_k \quad (4)$$

where s denotes the number of pixels representing a halation and being contained in the domain A31, and Xk and Yk denote x and y coordinates representing the positions of the halation contained in the domain A31.

Moreover, a regression line is calculated from the distribution of pixels, which represent the halation and being contained in the domain A31, according to the following expression (5):

$$y = \frac{Vxy}{Vx}(x - \bar{x}) + \bar{y} \quad (5)$$

where $\bar{x}$ and $\bar{y}$ denote averages of x and y coordinates representing the positions of pixels that represent a halation and that are contained in a domain Aij, Vx denotes a variance of x coordinates, and Vxy denotes a covariance of x and y coordinates. $\bar{x}$ and $\bar{y}$, Vx, and Vxy are calculated according to the following expressions (6) to (9):

$$\bar{X} = \frac{1}{s}\sum_{k}^{s} X_k \quad (6)$$

$$\bar{Y} = \frac{1}{s}\sum_{k}^{s} Y_k \quad (7)$$

$$Vx = \frac{1}{s}\sum_{k}^{s}(X_k - \bar{X})^2 \quad (8)$$

$$Vxy = \frac{1}{s}\sum_{k}^{s}(X_k - \bar{X})(Y_k - \bar{Y}) \quad (9)$$

A vector Vr orthogonal to the regression line is expressed using the variance Vx and covariance Vxy as follows:

$$Vr = (Vxy, -Vx) \quad (10)$$

Figure 14:
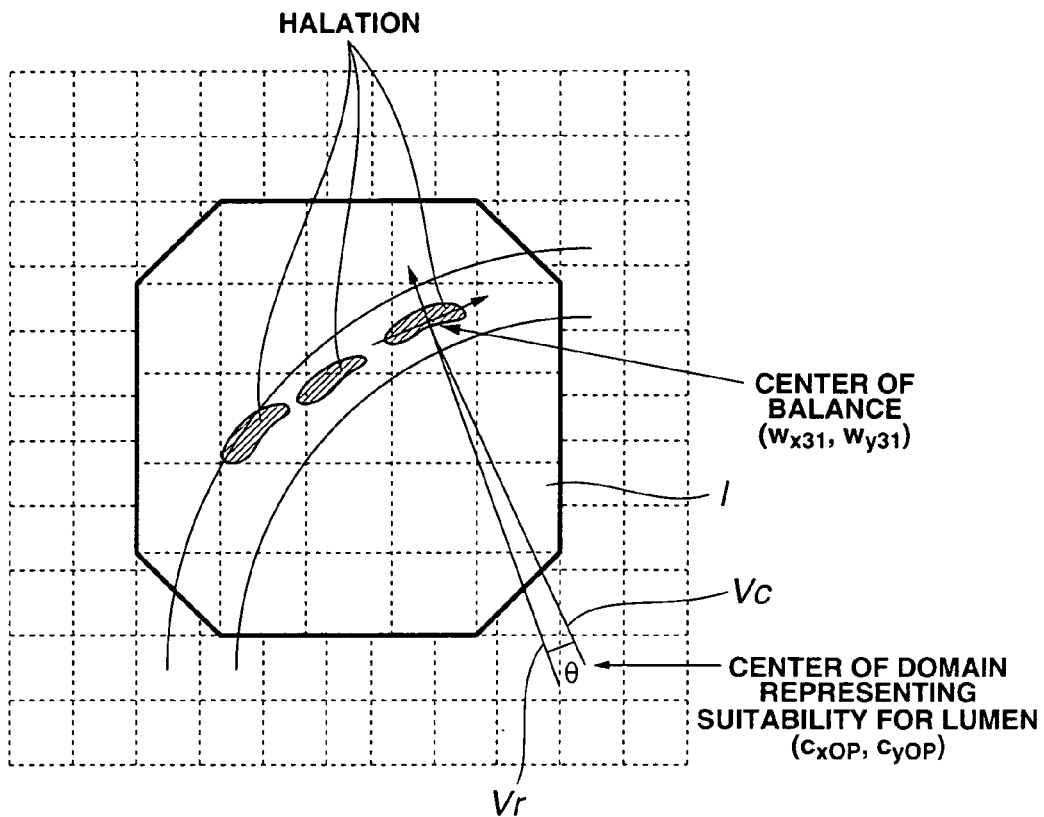
FIG. 14 is an explanatory diagram concerning detection of an endoscope inserting direction performed by the endoscope inserting direction detecting apparatus in accordance with the second embodiment of the present invention.

Moreover, a vector Vc whose initial point lies at the position of the center Cop(Cxop, Cyop) of a domain representing suitability for a lumen, which is shown in FIG. 14, and whose terminal point lies at the position of the center of balance (Wx31, Wy31) is calculated according to the following expression (11):

$$Vc = W_{31} - C_{op} = (W_{x31} - C_{xop}, W_{y31} - C_{yop}) \quad (11)$$

Furthermore, an angle θ at which the vector Vr and vector Vc meets is calculated as an inner product according to the following expression (12):

$$\cos\theta = \frac{Vr \cdot Vc}{|Vr||Vc|} \quad (12)$$

As shown in FIG. 14, as the angle θ approaches 0, the probability that a domain representing suitability for a lumen lies in a direction determined with the shape of a halation increases. The shape of a halation is thought to be useful in detecting the position of a lumen. An appropriate threshold θth1 is determined, and the sum total of domains Aij causing the angle θ to be smaller than the threshold θth1 is calculated.

As mentioned above, whether the shape of a halation is useful in detecting the position of a lumen can be judged, and the direction of a lumen can be estimated highly precisely.

Next, an endoscope inserting direction detecting apparatus in accordance with a third embodiment of the present invention will be described in conjunction with FIG. 15 to FIG. 22.

Figure 15:
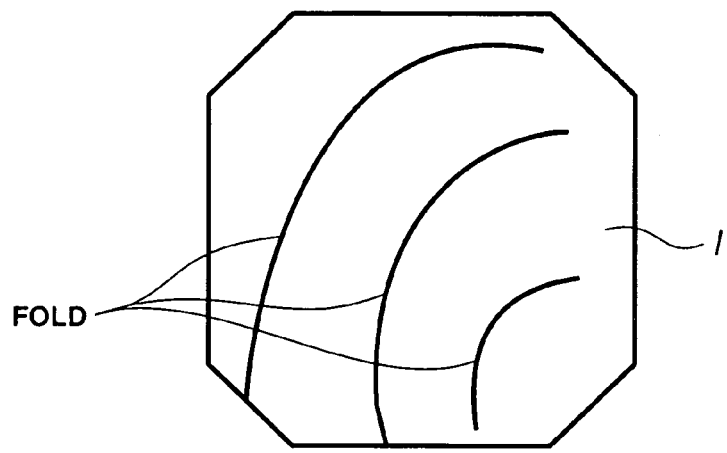
FIG. 15 is an explanatory diagram showing an image picked up image to be treated by an endoscope inserting direction detecting apparatus in accordance with a third embodiment of the present invention.
Figure 16:
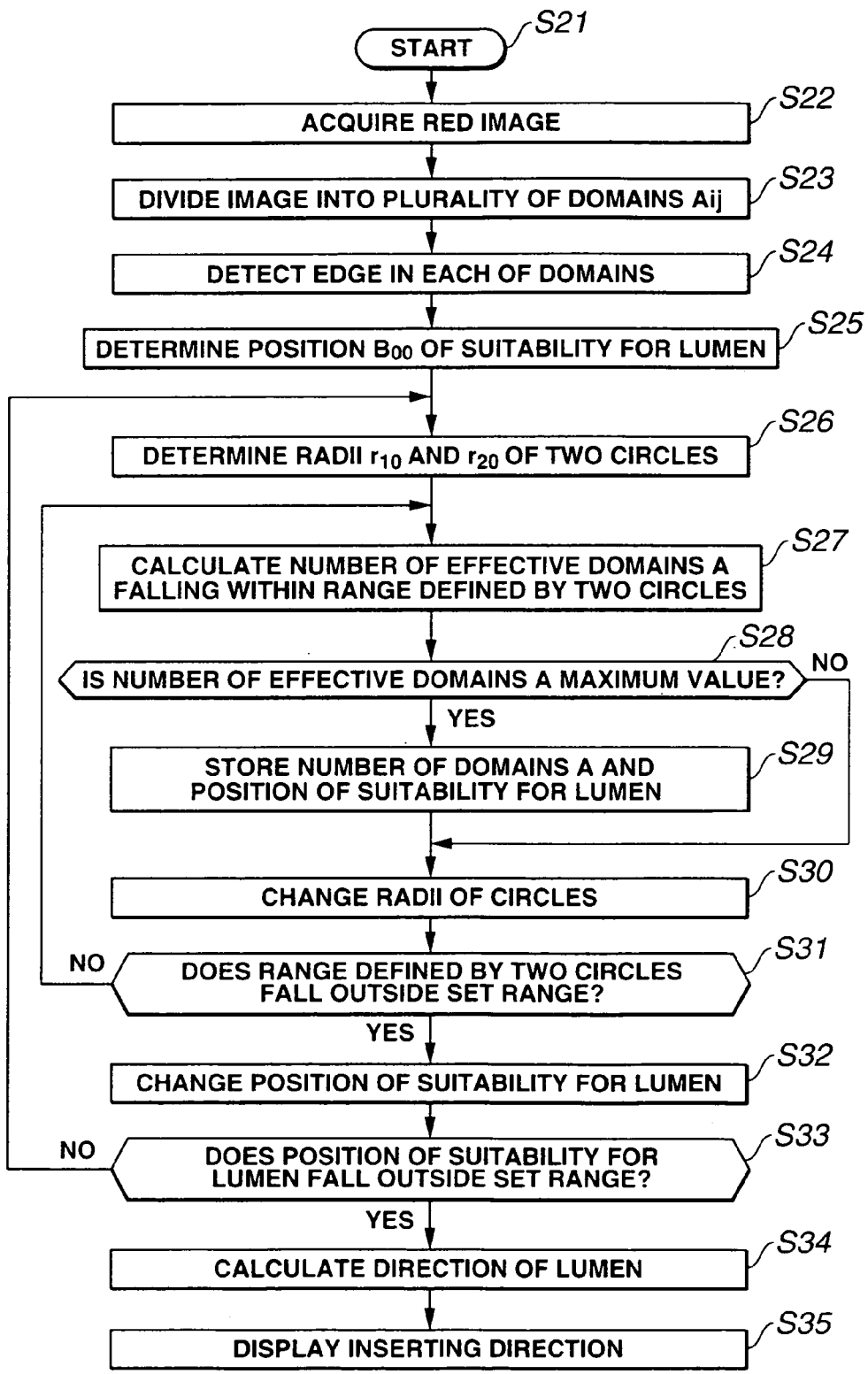
FIG. 16 is a flowchart describing actions to be performed by the endoscope inserting direction detecting apparatus in accordance with the third embodiment of the present invention.
Figure 17:
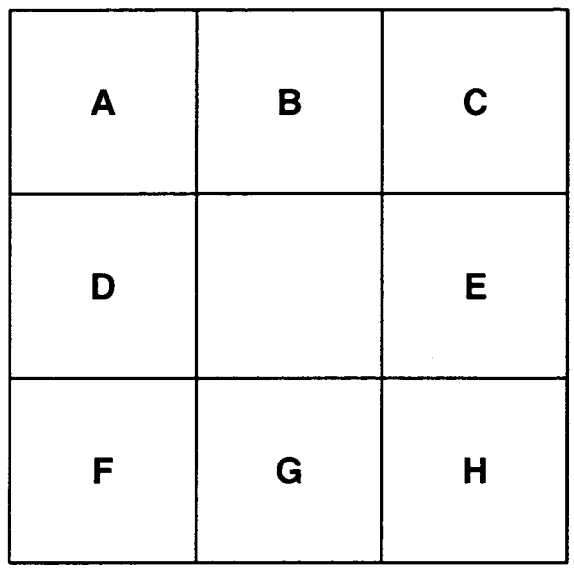
FIG. 17 is an explanatory diagram concerning detection of representatives of an edge from an endoscopic image which is performed by the endoscope inserting direction detecting apparatus in accordance with the third embodiment of the present invention.
Figure 18:
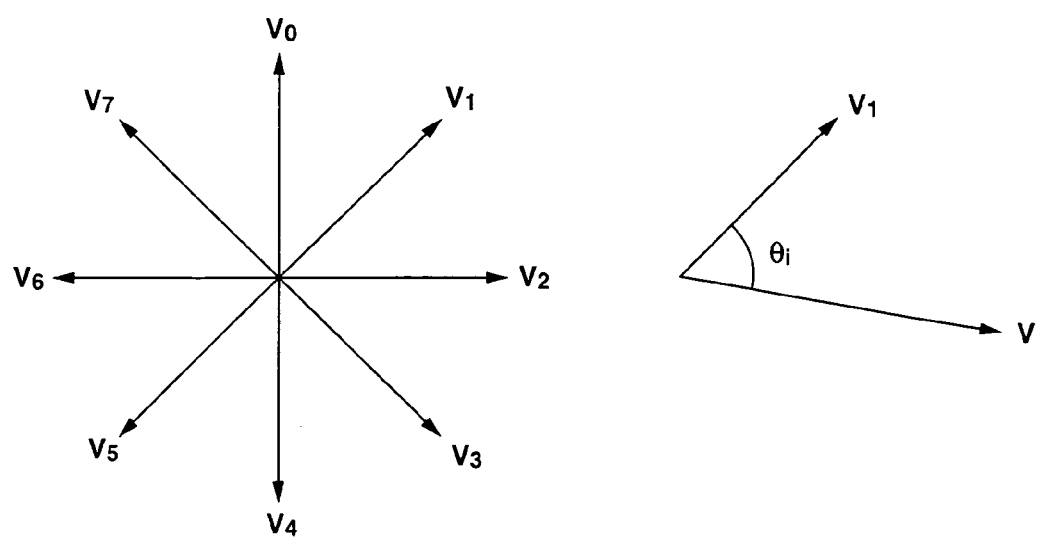
FIG. 18 is an explanatory diagram concerning classification of directions of representatives of an edge detected from an endoscopic image which is performed by the endoscope inserting direction detecting apparatus in accordance with the third embodiment of the present invention.
Figure 19:
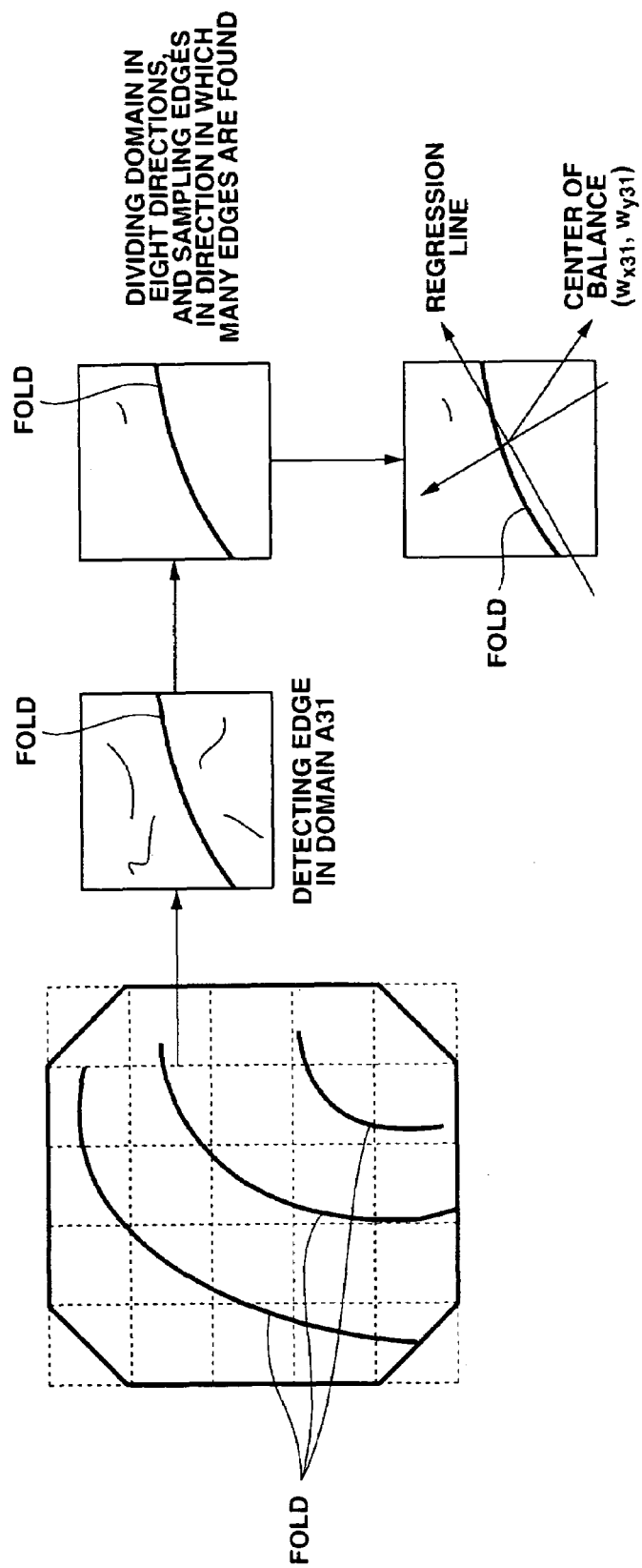
FIG. 19 is an explanatory diagram concerning the distribution of representatives of an edge sampled from an endoscopic image by the endoscope inserting direction detecting apparatus in accordance with the third embodiment of the present invention.
Figure 20:
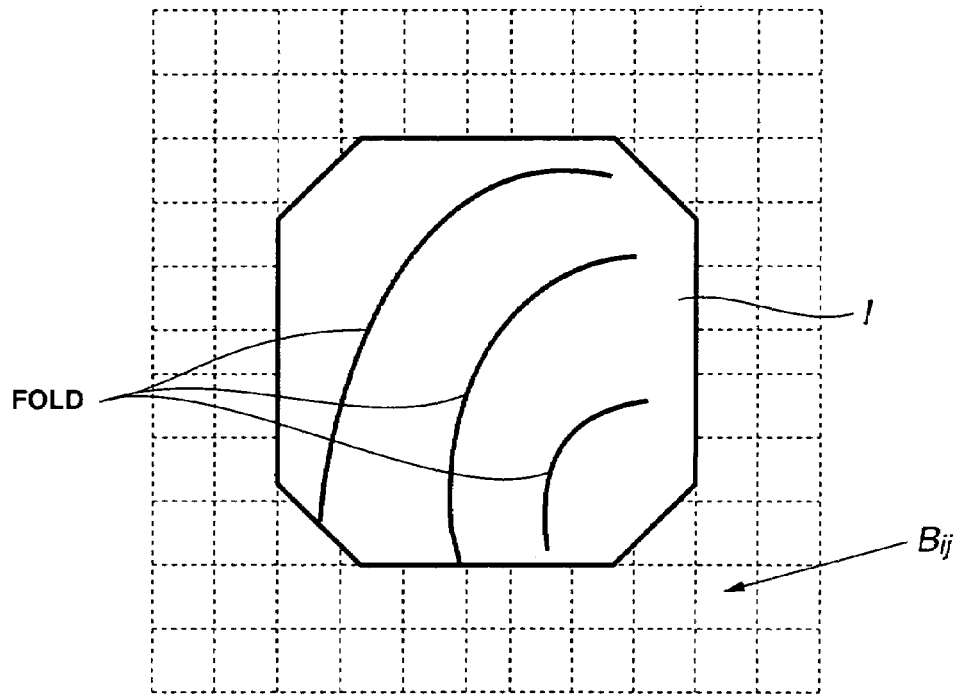
FIG. 20 is an explanatory diagram showing domains representing suitability for a lumen from an endoscopic image by the endoscope inserting direction detecting apparatus in accordance with the third embodiment of the present invention.
Figure 21:
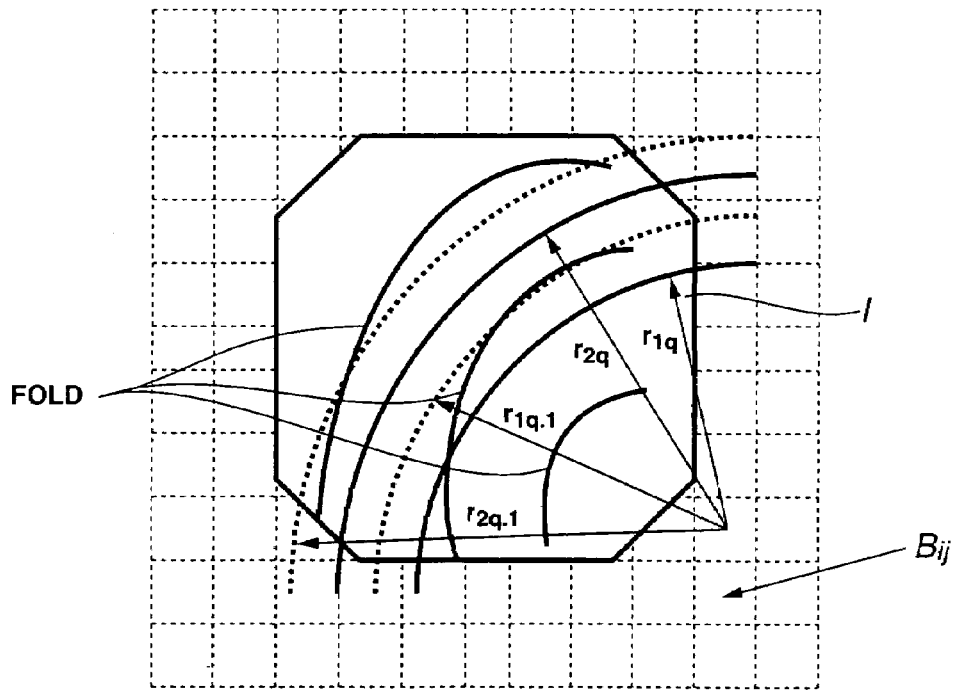
FIG. 21 is an explanatory diagram concerning selection of a domain representing suitability for a lumen, from an endoscopic image to be performed by the endoscope inserting direction detecting apparatus in accordance with the third embodiment of the present invention.

FIG. 15 is an explanatory diagram showing an image picked up image to be treated by the endoscope inserting direction detecting apparatus in accordance with the third embodiment of the present invention. FIG. 16 is a flowchart describing actions to be performed by the endoscope inserting direction detecting apparatus in accordance with the third embodiment of the present invention. FIG. 17 is an explanatory diagram concerning detection of an edge in an endoscopic image which is performed by the endoscope inserting direction detecting apparatus in accordance with the third embodiment of the present invention. FIG. 18 is an explanatory diagram concerning classification of directions of pixels, which represent an edge and are detected from an endoscopic image, that is performed by the endoscope inserting direction detecting apparatus in accordance with the third embodiment of the present invention. FIG. 19 is an explanatory diagram concerning the distribution of pixels that represent an edge and that are sampled from an endoscopic image by the endoscope inserting direction detecting apparatus in accordance with the third embodiment of the present invention. FIG. 20 is an explanatory diagram showing domains representing suitability for a lumen from an endoscopic image by the endoscope inserting direction detecting apparatus in accordance with the third embodiment of the present invention. FIG. 21 is an explanatory diagram concerning selection of a domain representing suitability for a lumen which is performed based on an endoscopic image by the endoscope inserting direction detecting apparatus in accordance with the third embodiment of the present invention. FIG. 22 is an explanatory diagram concerning determination of an inserting direction within a lumen which is performed based on an endoscopic image by the endoscope inserting direction detecting apparatus in accordance with the third embodiment of the present invention.

Incidentally, the configuration of the endoscope inserting direction detecting apparatus in accordance with the third embodiment is identical to that of the endoscope inserting direction detecting apparatus in accordance with the first embodiment. A difference lies in detection of the direction of a lumen that is performed by the computer 20.

The third embodiment focuses on the fact that the wall of the large intestine has annular folds and an endoscope inserting direction, in which an endoscope should be further inserted, can be judged from how the folds are depicted in an endoscopic image.

As mentioned previously, arc-shaped folds are, as shown in FIG. 15, depicted in an endoscopic image with the insertion unit 3 of the endoscope 1 inserted into a lumen as shown in FIG. 4.

The possibility that a lumen is found in a direction equivalent to the direction of the center of a circle including an arc defined by a representation of an arc-shaped fold is as high as the possibility that a lumen is found in a direction equivalent to the direction of the center of a circle including an arc defined by an arc-shaped halation and that is employed in the first embodiment. The representation of an arc-shaped fold is therefore adopted as information in judging an endoscope inserting direction.

Referring to FIG. 16, a description will be made of detection of an inserting direction within a lumen, in which an endoscope should be further inserted, using an endoscopic image that depicts the annular folds on the intestinal wall.

The CPU 23 included in the inserting direction detecting apparatus 12 reads an inserting direction detection program, which utilizes pixels representing folds on the wall of the large intestine, at step S21. At step S22, a red component of a received RGB image signal representing an endoscopic image is acquired in the same manner as that is in the first embodiment. Alternatively, similarly to the aforesaid first embodiment, a green component, a blue component, or a luminance component of an RGB image signal may be employed.

According to the red image signal acquired at step S22, a red image is displayed as an endoscopic image on the display device 21. At step S23, similarly to the first embodiment described in conjunction with FIG. 8, the endoscopic image is divided into a plurality of domains Aij ($0 \leq i<1$, $0 \leq j<m$).

At step S24, a gradient vector whose direction corresponds to the direction of each of pixels that constitute each of the domains Aij and that represent the edge of a fold is defined, and the magnitude of the gradient vector is calculated. Specifically, as shown in FIG. 17, pixels having three pixels lined in rows and columns with a pixel, which represents a point on an edge, as a center pixel are sampled. The values of the pixels lined horizontally, vertically, and diagonally shall be A, B, C, D, E, F, G, and H. A derivative dx of a horizontal pixel value and a derivative dy of a vertical pixel value are calculated according to the following expressions (13) and (14):

$$dx=(C+E+H)-(A+D+F) \quad (13)$$

$$dy=(F+G+H)-(A+B+C) \quad (14)$$

Using the derivatives dx and dy of horizontal and vertical pixel values, a gradient vector V whose direction corresponds to the direction of each of pixels representing an edge can be expressed as follows:

$$V=(dx, dy) \quad (15)$$

Based on the gradient vector V calculated according to the expression (15), the magnitude of each of pixels representing an edge is provided as follows:

$$|V|=\sqrt{dx^2+dy^2} \quad (16)$$

Thereafter, since a domain Aij contains not only pixels representing the edge of a fold but also pixels representing the edge of a vessel or the like that causes a noise, the pixels representing the edge of the fold are sampled according to a method described below.

The magnitude of each of pixels representing the edge of a fold, $|V|$, tends to get larger than that of each of pixels representing the edge of a vessel or the like. Therefore, an appropriate threshold $|V|thl$ is determined in order to sample pixels whose magnitudes are larger than the threshold.

Moreover, as shown in FIG. 18, eight vectors Vi (where i denotes 0, 1, etc., or 7) whose directions are different from one another are defined. The directions of pixels that represent an edge and that are sampled based on the threshold are classified into any of the eight directions. An angle $\theta i$ at which the gradient vector V of a sampled pixel and each of the vectors Vi having eight different directions meet is calculated according to an expression (17). A vector whose direction minimizes the angle $\theta i$ (vector whose direction is one of the eight directions) is detected. Thus, the directions of the sampled pixels representing an edge is classified into any of the eight directions.

$$\cos\theta_i = \frac{V \cdot V_i}{|V||V_i|} \quad (17)$$

The directions of pixels that represent edges and that are contained in a domain Aij and sampled based on the threshold are classified into the eight directions. Only the largest number of pixels classified into the same direction is adopted, whereby the pixels representing the edge of a vessel or the like that cannot be excluded using the threshold are deleted.

Furthermore, pixels contained in a small domain and representing the edge of a fold are presumably distributed linearly. According to a method similar to the one employed in the second embodiment, the distribution of sampled pixels representing an edge is checked as shown in FIG. 19.

After the pixels representing the edge of a vessel or the like are removed as mentioned above, the coordinates of the positions of the pixels representing the edge of a fold are used to calculate a center of balance, a regression line, and a vector orthogonal to the regression line.

A variance $\sigma 1$ of pixels that represent an edge and that are distributed in the direction of the regression line, and a variance $\sigma 2$ of pixels that represent an edge and that are distributed in a direction orthogonal to the direction of the regression line are calculated. Whether a ratio $\gamma$ of the variance $\sigma 2$ to the variance $\sigma 1$, that is, $\sigma 2/\sigma 1$ is smaller than an appropriate threshold $\gamma thl$ is judged. Thus, whether the pixels representing an edge are the pixels representing the edge of a fold is judged.

Thereafter, at step S25, the CPU 23 defines, as indicated with dot lines in FIG. 20, domains Bij ($0 \leq i<0$, $0 \leq j<P$) representing suitability for a lumen on the perimeter of an endoscopic image. At step S26, two circles r1q and r2q having different radii and having centers thereof located at the position of the center of a domain Bij representing suitability for a lumen are defined as shown in FIG. 21.

After the two circles are defined at step S26, the number of domains Aij representing the edge of a fold and falling within a range defined by the two circles is calculated. At this time, as shown in FIG. 22, an angle $\theta$ at which a vector orthogonal to a regression line calculated using the coordinates of the positions of pixels that are contained in each of the domains Aij and a vector whose direction corresponds to the direction to the center of the domain representing suitability for a lumen meet is calculated. If the angle $\theta$ is smaller than an appropriate threshold $\theta thl$, the domain Aij is judged as a domain representing the useful edge of a fold. Thus, the sum total of such domains Aij is calculated.

Thereafter, at step S28, the CPU 23 judges whether the number of domains Aij calculated at step S27 is a maximum value. If the number of domains Aij is judged as the maximum value, the number of domains Aij and the position Bij of suitability for a lumen are stored at step S29.

If the number of domains Aij is judged not to be the maximum value at step S28, or if storing the number of domains Aij and the position Bij of suitability for a lumen at step S29 is completed, the radii of the two circles are, as shown in FIG. 21, changed to r1q+1 and r2q+1 respectively at step S30. At step S31, whether the two circles whose radii are changed to r1q+1 and r2q+1 respectively at step S30 extend inside the domains Aij of an endoscopic image is judged. If the two circles extend inside the domains Aij of the endoscopic image, control is returned to step S27. Step S27 to step S30 are resumed. If the two circles extend inside the domains Aij of the endoscopic image, the position of suitability for a lumen is changed to another at step S32.

Thereafter, whether the position of suitability for a lumen into which the previous position is changed at step S32 falls outside a range of positions of suitability for a lumen, that is, the whole of domains Bij representing suitability for a lumen. If the position of suitability for a lumen falls within the whole of domains Bij representing suitability for a lumen, control is returned to step S26. Step S26 to step S32 are resumed. If the position of suitability for a lumen is judged to fall outside the whole of domains Bij representing suitability for a lumen, the domains representing suitability for a lumen shown in FIG. 11 are grouped into, for example, eight domains Di ($0 \leq i < 8$) at step S34 in the same manner as those in the first embodiment. A domain Di containing the new position of suitability for a lumen into which the previous position thereof is changed at step S32 is detected. At step S35, the direction of a lumen is estimated from the detected domain Di and displayed on the perimeter of the endoscopic image as shown in FIG. 12.

According to the third embodiment, the range defined by two circles is narrowed. Consequently, a representation of a fold shaped more greatly like an arc can be detected.

Moreover, since domains representing suitability for a lumen are defined finely, the position of a lumen can be estimated highly precisely.

According to the third embodiment, only a representation of the edge of a fold on the wall of a lumen that is useful in detecting the direction of a lumen is detected. The direction of the lumen can be readily and accurately detected based on the representation of the edge.

The embodiments of the present invention have been described so far. The present invention is not limited to the embodiments. Needless to say, many variations can be made without a departure from the spirit of the present invention.

INDUSTRIAL APPLICABILITY

As described above, according to an endoscope inserting direction detecting apparatus, an endoscope inserting direction detecting system, and an endoscope inserting direction detecting method in which the present invention is implemented, the position of a lumen and an endoscope inserting direction can be accurately detected based on an endoscopic image. When the inserting direction is displayed together with the endoscopic image on a display device, an endoscope can be inserted without a patient discomfort. Thus, the present invention will be adapted to endoscopic examination of an intracavitary region or endoscopic treatment thereof.

The invention claimed is:

1. An endoscope inserting direction detecting system comprising:
   endoscopic image domain dividing means for dividing an endoscopic image, which is imaged and produced by an endoscope inserted into a body cavity, into a plurality of domains;
   pixel sampling means for comparing the values of pixels constituting each of the domains, into which the endoscopic image domain dividing means divides the endoscopic image, with a threshold, and for sampling the distribution of pixels whose values are equal to or larger than the threshold;
   suitability-for-lumen position defining means for defining domains representing suitability for a lumen position;
   direction-of-lumen estimating means for defining a plurality of circles, which have different radii, over the domains representing suitability for a lumen and being defined by the suitability-for-lumen position defining means and the domains of the endoscopic image, and for estimating the direction of a lumen from the distribution of pixels which are sampled by the pixel sampling means because the values thereof are equal to or larger than the threshold and which are placed between the plurality of circles;
   inserting direction determining means for determining an endoscope inserting direction over the domains, which represent suitability for a lumen position, on the basis of the direction of a lumen estimated by the direction-of-lumen estimating means; and
   inserting direction display means on which an inserting direction is displayed together with the endoscopic image on the basis of the endoscope inserting direction determined by the inserting direction determining means.

2. An endoscope inserting direction detecting system according to claim 1, wherein the pixel sampling means samples pixels that represent a halation caused by specular reflection in the body cavity or pixels that represent the edge of a fold on the inner wall of the body cavity.

3. An endoscope inserting direction detecting system according to claim 1, wherein the direction-of-lumen estimating means estimates the direction of a lumen, which is useful in determining an inserting direction, from a difference in an angle between a vector whose initial point lies at the position of a center of balance in the distribution of pixels sampled by the pixel sampling means and whose terminal point lies at the position of the center of a domain representing suitability for a lumen position out of all the domains defined by the suitability-for-lumen position defining means, and a vector orthogonal to a regression line expressing the distribution of pixels.

4. An endoscope inserting direction detecting system according to claim 1, wherein the direction-of-lumen estimating means calculates a gradient vector that expresses each of pixels representing the edge of a fold and being sampled by the pixel sampling means, and estimates the direction of a lumen from the distribution of pixels that are expressed with gradient vectors having the same direction and that represent the edge.

5. An endoscope inserting direction detecting system according to claim 1, wherein the centers of the plurality of circles having different radii and extending over the domains, which represent suitability for a lumen position and are defined by the suitability-for-lumen position defining means, and the domains of the endoscopic image are located in the same domain representing suitability for a lumen position.

6. An endoscope inserting direction detecting system according to claim 1, wherein the direction of a lumen estimated from the distribution of pixels, of which values are equal to or larger than the threshold and which are placed between the plurality of circles having different radii, by the direction-of-lumen estimating means corresponds to the direction of the position at which the centers of the plurality of circles lie.

* * * * *